United States Patent [19]

Cotton

[11] Patent Number: 4,565,552
[45] Date of Patent: Jan. 21, 1986

[54] METHOD OF PRODUCING BIOGAS AND COMPOST

[76] Inventor: Armand Cotton, 183 route de Mon Idée, 1253 Crête, Vandoeuvres, Geneva, Switzerland

[21] Appl. No.: 669,578

[22] Filed: Nov. 7, 1984

[30] Foreign Application Priority Data

Nov. 9, 1983 [CH] Switzerland .................... 6033/83

[51] Int. Cl.[4] .................... C02F 3/30; C05F 11/08; C12P 5/02
[52] U.S. Cl. ........................... 48/197 A; 71/9; 71/10; 210/603; 210/607; 210/613; 210/630; 435/167; 435/801
[58] Field of Search .............. 48/197 A, 209, 197 R; 210/603, 607, 609, 612, 613, 623, 624, 626, 630; 435/167, 801; 71/9, 10

[56] References Cited

U.S. PATENT DOCUMENTS

| | | | |
|---|---|---|---|
| 1,456,557 | 5/1923 | Imhoff | 435/167 |
| 1,930,457 | 10/1933 | Pruss | 210/613 |
| 2,315,577 | 4/1943 | Bach | 210/613 |
| 2,572,767 | 10/1951 | Schlenz | 210/612 |
| 2,875,151 | 2/1959 | Davidson | 210/605 |
| 3,933,628 | 1/1976 | Varani | 210/603 |

Primary Examiner—Jay H. Woo
Assistant Examiner—Joye L. Woodard
Attorney, Agent, or Firm—Steele, Gould & Fried

[57] ABSTRACT

In the mesophile production of biogas, the temperature of the liquid used during anaerobic, methanogenic, fermentation is raised to the required temperature (about 35° C.) by aerobically prefermenting solid substrate at substantially ambient temperature and of appropriate moisture content to raise its temperature to a temperature greater than that required for the anaerobic, methanogenic, fermentation. Thereafter flooding the fermenting solid substrate with the liquid at substantially ambient temperature to increase the temperature of the liquid by heat exchange, and then removing the liquid and storing it in a heat insulated environment to reduce the moisture content of the solid substrate to a suitable degree. The above steps of aerobic prefermenting and flooding are repeated until the liquid has reached the required temperature, and then leaving the liquid in situ to enable anaerobic methanogenic fermentation to take place. In so doing the supply of external heat for the initial warming up of the substrate may be dispensed with, thereby improving the efficiency of the method.

4 Claims, 3 Drawing Figures

METHOD OF PRODUCING BIOGAS AND COMPOST

BACKGROUND OF THE INVENTION

This invention relates to a method of and to a plant for producing biogas and compost.

To produce biogas with fermentable solid organic matter, such as manure, the matter must first go through a methanogenic fermentation, i.e. a fermentation producing methane, the main constituent of biogas. Such fermentation may only occur in an anaerobic (airless and lightless) environment and requires a certain temperature which varies depending on whether the fermentation is to be psychrophile (between 10° and 22° C.), mesophile (between 22° and 45° C.) or thermophile (between 45° and 75° C.). The anaerobic environment is obtained by submerging the organic matter with a liquid. For mesophile fermentation and thermophile fermentation, the required temperature is achieved by heating the mass of matter and liquid with ad hoc means. This may require a considerable input of outside heat thereby correspondingly decreasing the energetic efficiency of the method. This is a long drawn out operation. Further, when the matter is heaped, as is the case with a batch-feed process involving vats, it is difficult if not impossible to achieve appropriate heating of the matter thus leading to inefficient fermentation.

SUMMARY OF THE INVENTION

An object of the invention is to provide a method of producing biogas at mesophile fermentation temperature that can be started up without external heat.

As is known, fermentable solid organic matter, such as manure, when moist and when exposed to air, ferments with a rapid increase in temperature. This is a fermentation that brings into play micro-organisms (bacteria) that are different from those responsible for methanogenic (or anaerobic) fermentation. Unlike the latter, aerobic fermentation is exothermic and does not give off biogas.

The invention consists in taking advantage of this heat generating phenomenon to start up a mesophile process so as to avoid having to resort to external heat. Aerobic fermentation also has the advantage of heating the matter more uniformly than could be achieved with external heat.

BRIEF DESCRIPTION OF THE DRAWINGS

In the accompanying drawings, given by way of example.

DETAILED DESCRIPTION

Figure 1:
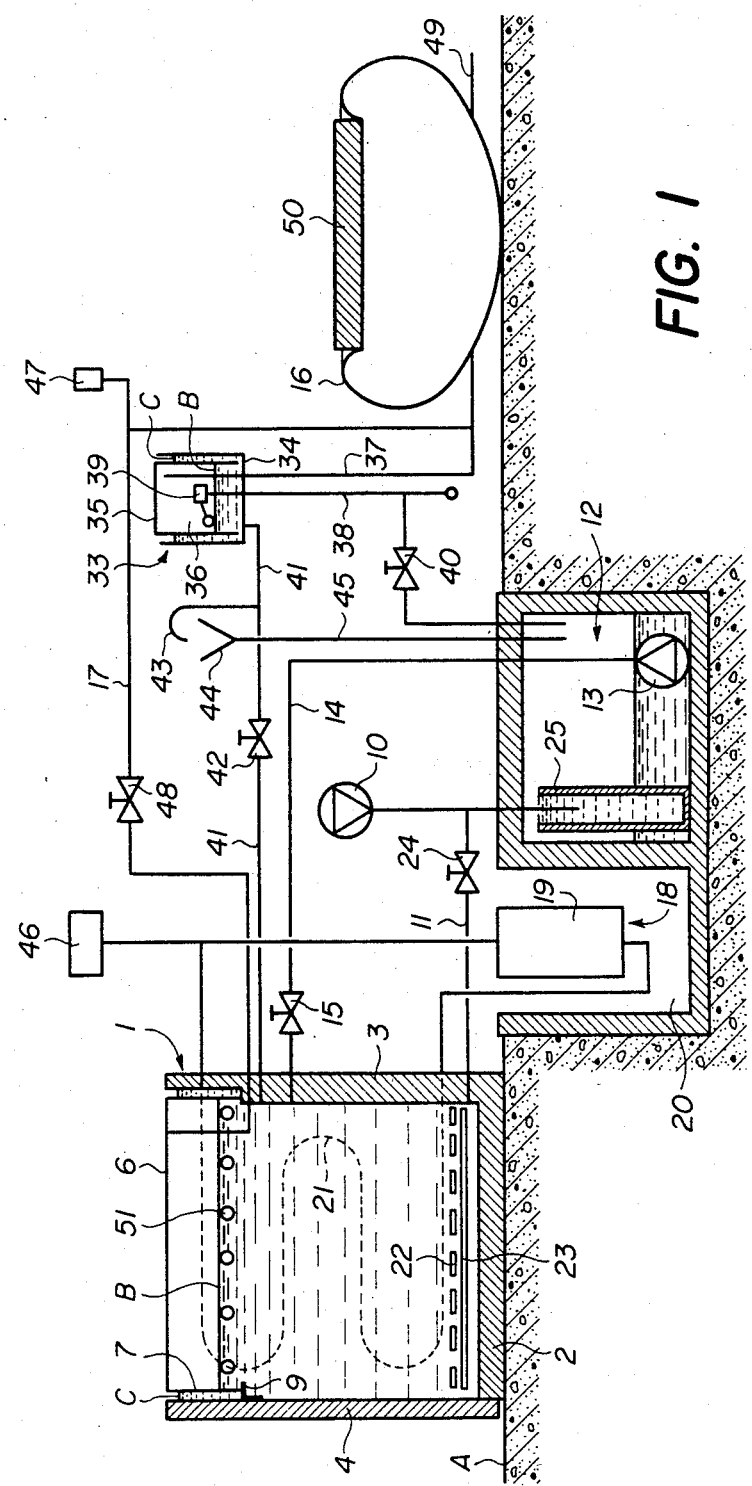
FIG. 1 is an overall view, in longitudinal cross-section, of an embodiment of a plant according to the invention.
Figure 2:
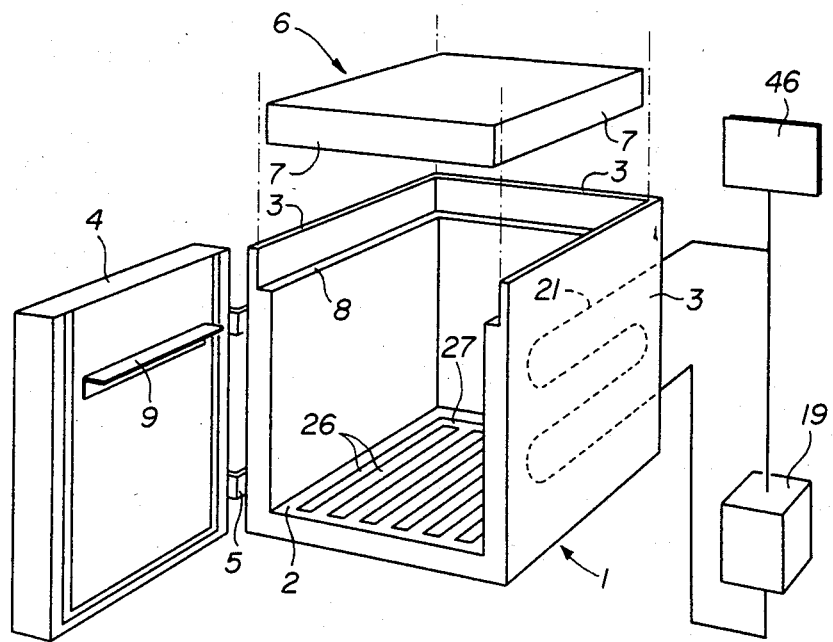
FIG. 2 is a perspective view of a digester used in the plant of FIG. 1, with a modified floor.

The plant shown in FIG. 1 comprises a digester (also called a fermentor) resting directly on the ground A and consisting of a parallelepipedic vat 1 made of concrete, metal or other impermeable and pressure-resistant material. The vat used here has a volume of about 4.5 m³ with a floor area of about 3 m². As shown in FIG. 2, the vat has four fixed elements, i.e. a floor 2 and three upright walls 3, and a lighweight, water-tight and pressure-resistant door 4 which opens by turning on hinges 5 or in any other way. Vat 1 is also provided with a onepiece impermeable lid 6 made of metal, of plastics or other suitable material, having downturned flanges 7 bearing on horizontal shoulders 8 provided in a common plane near the top of the three walls 3 on the inside thereof, and on a horizontal ledge 9 secured to the inside of door 4, level with shoulders 8.

The illustrated plant is particularly suited to small farms for the production of gas from manure (in particular cow, horse or pig manure) and other fermentable solid organic matter to be found on such farms (straw, vegetable leaves, grass, leaves, sawdust, wood shavings, etc.).

To put the plant into operation, the following procedure may for example be adopted:

1. Lid 6 is raised or removed and door 4 is opened.
2. Vat 1 is filled with, for instance, strawy manure by a tractor fitted at the front with handling means, e.g. a fork, the tractor entering vat 1 through the doorway. Each fork load is preferably spread, packed, particularly near the edges, and, if the matter is on the dry side, wetted. If the manure is bovine, no seeding with methanogenic bacteria is needed, such bacteria being naturally present in bovine manure. In other cases, seeding is needed either with bovine manure, sludge from sewage processing or ad hoc biological products.
3. Door 4 is closed and locked and loading is completed through the top with the matter being packed against the door while keeping shoulders 8 and ledge 9 clear.
4. Air is blown into vat 1 through floor 2 by a fan 10 via a duct 11 for about one day. With the substrate properly packed against walls 3 and door 4, the air is forced to rise through the substrate. This leads to aerobic fermentation (or digestion) of the substrate, and causing its temperature to rise, generally to between 60° and 75° C., but possibly higher, particularly at its centre.
5. After this heating, which takes about one day, the air blowing is stopped and the hot substrate is flooded with about 3.5 m³ of liquid manure and/or water at ambient temperature (say 12° C.) contained in a cistern 12, by means of a transfer pump 13 via a duct 14 fitted with a hand operated clock 15. The heat in the substrate then warms up the liquid by about 15° C. The increase in temperature of the liquid depends on the latter's starting temperature. The lower the starting temperature the greater the increase.
6. About 2.5 m³ of warmed up liquid is then drawn off through the floor 2 via duct 11 for storage in cistern 12. The remainder of the liquid, i.e. about 1 m³, is absorbed by the substrate.
7. When the substrate has sufficiently drained to enable air to be blown in (about half an hour), aerobic fermentation is started up again by switching on fan 10 to raise the temperature back to 60° C. or more. This air blowing operation lasts for about two days.
8. The substrate is again flooded with the warmed up liquid stored in cistern 12. Since the temperature difference between the substrate and the liquid is now less, the temperature of the liquid will rise to a lesser extent, i.e. about 10° C.
9. If the liquid at the end of this heating operation reaches, as would be the case with the given example, a temperature of about 35° C., this being the optimal temperature for mesophile methanogenic fermentation, lid 6 is put back on vat 1 by clamping it down with fasteners not shown, the mesophile methanogenic fermentation is allowed to take place, such fermentation lasting for example from four to eight weeks depending on the ultimate objective, and the gas that is given off is collected in a gas-holder (or gasometer) 16 of variable volume via a duct 17. One objective may be the maximum production of biogas; in this case the fermentation process is stopped after already four weeks to start up a fresh vatful. Another objective may rather be geared to the production of compost, in which case the fermentation process is continued till it is nearly fully exhausted, i.e. for about eight weeks. Intermediate fermentation times can of course also be considered.

10. But should the liquid at the end of operation (8), say after a quarter of an hour or so, not have reached a temperature of about 35° C. (in particular in winter), operations (6), (7) and (8) are repeated as many times as necessary to reach the required temperature before proceeding with operation (9). For a third aerobic fermentation operation, air is blown in for about three days. The rise in temperature of the liquid this time will only be about 4° to 6° C. For a fourth fermentation operation (rarely needed) air is blown in even longer and the temperature rise wil be even slighter.

The above indicated times are all approximate, applicable only to the experimental plant described here. These times may therefore vary from one plant to the next, and are dependent on the kind of substrate being processed and on its moisture content. The same applies to the temperature rises achieved with each aerobic fermentation; these rises also depend on atmospheric conditions.

This succession of aerobic fermentation operations (which may be termed prefermentation operations) are only needed when starting up the plant to raise the liquid needed for the methanogenic fermentation to the required temperature. As will be noted, these prefermentation operations require no external heat input and are carried out in the same vat as the methanogenic fermentation.

As will be apparent from operation (6) a considerable amount of liquid is absorbed during the first flooding of the substrate. During the second flooding, the substrate will absorb a lesser amount of liquid and during the third flooding the substrate will absorb a still lesser amount of liquid. Consequently, the amount of liquid having to be introduced into vat 1 for the subsequent floodings decreases accordingly and less and less liquid therefore needs to be heated.

It is best to have a temperature a few degrees (say 3° C.) more than the optimal temperature of 35° C., to provide a safety margin against the inevitable heat losses that occur when starting up the plant.

At the end of the methanogenic fermentation, lid 6 is removed, the hot liquid is drawn off for storage in cistern 12, door 4 is opened, vat 1 is emptied by means of a tractor fitted at the front with a manure fork, operations (2) to (4) are repeated, the blowing in of air is stopped, the ferment-laden hot liquid stored in cistern 12 is reintroduced into vat 1 after having first added thereto make-up liquid at ambient temperature to provide the required volume, lid 6 is put back on vat 1, a fresh mesophile methanogenic fermentation is allowed to take place, and the gas that is given off is again collected. This cycle of operations may be repeated indefinitely during the lifetime of the plant.

To reduce heat losses to a minimum, vat 1 and cistern 12 should be insulated as much as possible, e.g. with panels of polystyrene and/or glass wool. However efficient the insulation, heat losses will nevertheless occur. To compensate those of vat 1 and hence maintain the optimal temperature of 35° C. inside the latter during mesophile anaerobic fermentation (which generates only very little heat), the plant is further provided wth a thermosiphon 18 having a water-heater 19 disposed below the level of ground A (and hence of vat 1) in a pit 20, one or more coils 21 for circulating the heat-carrying water in one or more of vat walls 3, and an expansion vessel 46. By being embedded in walls 3, coils 21 enable a tractor with its fork to operate in vat 1 without endangering the heating system. The water-heater, which burns biogas to maintain the optimal production temperature, only uses a small proportion of the gas produced (a normal average of about 10%). The use of a thermosiphon for heating purposes saves having to provide a circulation boosting pump and saves the energy required to drive it.

When the site lends itself to it, one or more solar energy captors may be provided in parallel with the water-heater to improve the overall efficiency of the plant.

When the biogas is used as fuel for a motor driving, for instance, an electricity generator, the cooling water for the motor may be circulated in coils 21.

As already explained, the air blown into vat 1 and the liquid drained therefrom flow through its floor 2. As shown in FIG. 1, floor 2 may consist of removable grating elements 22 made of metal, concrete or wood that are supported a certain distance above the foundation of the vat by angle irons 23 secured to walls 3, to provide a space enabling, on the one hand, the liquid to be drawn off via duct 11 into cistern 12 and, on the other hand, the air being blown in to be distributed beneath the whole of the mass of substrate stacked in vat 1.

As shown in FIG. 1, duct 11 comprises a substantially horizontal portion fitted with a hand operable cock 24 and a substantially vertical portion. The top end of the vertical portion is connected to a fan 10 while its bottom end terminates in a receptacle 25 constantly filled with liquid, disposed in cistern 12. This vertical portion dips into the liquid of receptacle 25 sufficiently deeply to prevent air from the fan 10 to flow out of the bottom end instead of into vat 1. Further, fan 10 should be placed at a level sufficiently high so as not to be reached by liquid flowing out of vat 1 into cistern 12 (via receptacle 25).

While vat 1 is being filled by means of pump 13, and throughout methanogenic fermentation, duct 11 is kept closed by means of cock 24.

At the start of the prefermentation operations air, and liquid being drained out of vat 1, counter-flow through the horizontal portion of duct 11.

Grating elements 22 firstly being expensive, secondly generally not being durable and thirdly having to be removed to clean out the space beneath floor 2 before each reloading operation, it is preferred to replace them with a fixed grating such as that shown in FIG. 2.

This fixed grating can be produced much more cheaply, on the spot, when building the vat. It comprises a plurality of parallel grooves 26 about 3 cm wide and from 6 to 8 cm deep (to provide a slope), that are connected by a transverse collector groove 27 of similar width but deeper at the rear of the vat and communicating with duct 11. Grooves 26 are spaced about 7 cm from each other.

The production of the grating requires first making a mould (or negative) with a material that can readily be destroyed or extracted once the concrete has been poured (e.g. expanded polystyrene), the solid parts of the mould corresponding to grooves 26 and 27 for the flow of air and liquid.

The mould is then laid on a roughly cast base layer of fresh concrete forming the vat foundation, and its hollow parts are then carefully filled with mortar.

Once the concrete and mortar have set, the material used for the mould is removed to provide grooves 26 and 27 in a floor 2 over which a tractor may be driven.

The grating being integral with the foundation, is most solid and highly durable. Also, the parallel grooves may, without any kind of dismantling, readily be cleaned with a scraper of simple design.

Door 4 is made of wood or other lightweight and rigid material. It is made fluidtight by a rigid sheet 28 of plastics material, e.g. PVC sheet material having a thickness of say 5 mm, lining the inner surface of the door to which it is secured by any suitable means such as adhesive or screws. The ledge 9, here formed by an angle iron, is welded to sheet 28.

Figure 3:
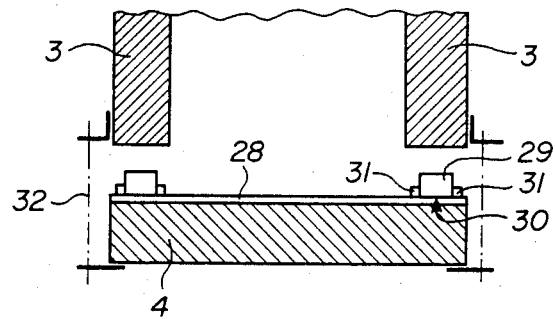
FIG. 3 is a horizontal cross-sectional view of the digester shown in FIG. 2, fitted with a hingeless door.

Fluidtightness between door 4 and the reminder of vat 1 is provided by a gasket consisting of a continuous strip 29 of foam, nipped in a holder 30. The foam is preferably relatively rigid. It should be formed of occluded cells and should be able to withstand attack from liquid manure. In the present case, the foam is natural rubber foam. Holder 30 is welded to sheet 28 opposite the edge of the vat's foundation and opposite the edges of the two adjacent walls 3 (FIG. 2) such that the foam is crushed to some extent against these edges when the door is closed. The edges should of course be very flat. Holder 30 may for example be formed of one or more rigid channel-section elements of plastics material which are fluidtightly welded to sheet 28 and which define a groove in which foam strip 29 is nipped, or, as shown in FIG. 3, may consist of pairs of spaced apart ribs 31 which are welded to sheet 28 and which are so shaped and arranged as to provide a nipping groove for strip 29. This nipping construction for strip 29 enables the latter to be readily replaced.

Door 4 is kept pressed against said edges by fasteners 32 (FIG. 2) set fairly close to one another, or in any other suitable way.

Fluidtightness between lid 6, on the one hand, and vat 1 and door 6, on the other hand, is provided by a hydraulic seal formed by the liquid used to flood the substrate in vat 1, in conjunction with the flanges 7 of lid 6 when the latter rests on shoulders 8 and ledge 9, insofar as the liquid is at a level higher than that of shoulders 8 and ledge 9 on opposite sides of flanges 7, and remains so throughout the methanogenic fermentation.

The gas given off by the substrate accumulates under lid 6 and sets up an over-pressure. This over-pressure manifests itself by a drop in the level B of the liquid inside lid 6 and a rise in the level C of the liquid outside lid 6. The gas causing this over-pressure passes into reservoir 16 via duct 17.

For the hydraulic seal to operate, the level B of the liquid inside lid 6 must not drop below a certain level otherwise gas escapes into the atmosphere by passing under flanges 7 of lid 6, and the level C of the liquid outside the lid must not rise above a certain level otherwise vat 1 overflows.

Now, in practice, level B varies with the variations in volume of the fermenting substrate (largely due to the digestion process) and with the variations in pressure of the gas in the network.

To maintain, despite these variations, level C outside lid 6 at a given maximum level and level B inside lid 6 at a given minimum level, the invention provides a level regulator 33. Regulator 33, which is located outside vat 1 at the same level as lid 6, comprises a tank 34 and a lid 35 having a downturned flange 36 bearing inside tank 34 on the bottom thereof, which bottom is at the same level as shoulders 8 and ledge 9 of vat 1. Flange 36 has the same height as flanges 7 of lid 6, and between the walls of tank 34 and flange 36 is provided a space similar to that between lid 6 and vat 1, such as to reconstitute on a smaller scale the hydraulic seal of the digester with its different liquid levels B and C due to the difference between the pressures existing inside and outside lid 6.

A pipe 37, connected to gas-holder 16, ends under lid 35 to set up inside the latter a pressure equal to that existing under digester lid 6, pressure equalization having already been established between gasholder 16 and the digester via duct 17. A second pipe, 38, feeds mains water to a ball-cock 39 regulating the minimum level of the liquid inside lid 35, and, via a hand operated cock 40, to cistern 12.

A third pipe 41, feeds make-up water to vat 1 from tank 34. Pipe 41 includes a hand operated cock 42 which is closed each time vat 1 is emptied and which is opened at the start of each subsequent methanogenic fermentation operation. Pipe 41 further includes, between tank 34 and cock 42, an overflow 43 which opens into the ambient air and which sets the maximum level of the liquid outside lids 6 and 35, thereby preventing tank 34 and vat 1 from overflowing. Liquid issuing from overflow 43 is collected in a funnel 44 to be conveyed to cistern 12 via pipe 45. Lid 35 is held in place by fastening means not shown.

The liquid may reach its maximum level firstly when the mass contained in the digester expands and secondly when the pressure of the gas in the network increases.

An expansion of the mass normally causes levels B and C of the liquid inside and outside lids 6 and 35 to rise equally. Although the rise in level C outside lids 6 and 35 is limited by overflow 43, level B inside lids 6 and 35 may however continue to rise. The height of flanges 7 and 36 of lids 6 and 35 must therefore be so dimensioned to take into account maximum expansion of the mass such as always to leave free spaces for the gas, the top ends of duct 17 and of pipe 37 ending in these spaces above the uppermost internal level.

A pressure increase, which occurs in any case as gas-holder 16 fills and which may additionally occur when gas-holder 16, here made of rubberized woven material, is heated by the sun, causes level B inside lids 6 and 35 to drop. In view of the ratio of the liquid surfaces inside and outside lids 6 and 35, a small drop in level B inside the lids normally causes a substantial rise in level C outside the lids. This could lead to both a prolonged discharge of liquid from overflow 43 to prevent outer liquid level C from exceeding the maximum level and to a prolonged flow of liquid into tank 34 from ball-cock 39 to prevent inner liquid level B from dropping below the minimum level. This state of affairs may be avoided by including in the gas network an over-pressure valve 47, e.g. in duct 17.

Duct 17 is also provided, between valve 47 and vat 1, with a manually operated cock 48 which is closed before removing lid 6 at the end of a methanogenic fermentation operation to prevent the gas stored in gas-holder 16 from escaping. Cock 48 is again opened when lid 6 is put back in place for the start of a new methanogenic fermentation operation.

The gas stored in gas-holder 16 may be conveyed by a duct 49 to various combustion points, including the burner of water-heater 19. For this the gas must have a minimum pressure, e.g. 8 millibars. To this end, a ballast 50 of appropriate weight is laid on top of the flexible gas-holder 16. This ballast ensures said minimum pressure from the moment storage begins. However, when gas-holder 16 is full, the pressure of the gas may be as high as 20 millibars or so.

During methanogenic fermentation the substrate contained in vat 1 tends to float. To prevent it from rising to the surface of the liquid, lid 6 is fitted with a plurality of grid-forming bars or tubes 51 at the level of the lower edges of flanges 7. By rendering the resulting grid solid (as by welding) with lid 6, separate handling of bars or tubes 51 can be avoided. Heat insulation for lid 6 is also incorporated in the latter thereby avoiding another separate handling operation.

The above described and illustrated method and plant may be modified in various ways. For instance, use may be made for the substrate of household refuse, once rid of non fermentable and non solid matter, and use may be made, by way of liquid, of sludge from sewage processing.

Instead of a single digester, the plant may comprise a battery of several digesters connected in parallel to gas-holder 16 to provide continuous production of gas, the number of digesters being dependent on the amount of available fermentable organic matter. In such a plant a single level regulator suffices, provided that the above mentioned liquid levels are the same for all digesters.

When deciding the number of digesters in such a plant, there should be provided an additional vat that produces no gas (e.g. four digesters when it is planned to have three operational) so as to have available one vat for receiving daily fresh manure. This avoids building up an outer heap of manure that will later need to be transferred into a vat once it has been cleared of its contents at the end of a cycle.

Under these conditions, the non productive vat can also be used as a container for warmed up liquid issuing from a digester being started up. The warmed up liquid would thus only briefly be passing through cistern 12 and the volume of the latter may therefore be substantially reduced, to e.g. 1 m$^3$, whatever number of vats 1 there are in the plant.

Duct 17 and pipe 37, instead of passing through the walls of vat 1 and tank 34, may pass through the tops of lids 6 and 35, in which case duct 17 and pipe 37 are made flexible at least near the lids to enable the latter to be manipulated.

In practice, the digesters have substantially larger volumes than indicated, e.g. several tens of cubic meters.

Instead of feeding mains water to level regulator 33, the latter may be supplied with liquid stored in cistern 12. Ball-cock 39 may also be replaced by a level detector controlling pump 13, the liquid from cistern 12 being conveyed into tank 34 via duct 14, vat 1 and pipe 41. In that case, the portion of pipe 38 extending into tank 34 can be dispensed with.

I claim:

1. A method of producing biogas and compost, which comprises the steps of (1) fermenting in an aerobic environment solid fermentable organic matter at substantially ambient temperature and of appropriate moisture content to raise its temperature to a temperature greater than that required for mesophile methanogenic fermentation in an anaerobic environment, (2) flooding the fermenting organic matter with liquid at substantially ambient temperature to increase the temperature of the liquid by heat exchange with the fermenting organic matter, (3) removing the liquid to store it in a heat insulated environment to reduce the moisture content of the matter to a suitable degree, (4) raising the temperature of said matter to said greater temperature by aerobic fermentation, (5) again flooding the matter with the stored liquid to raise the temperature of the latter still further by heat exchange with the fermenting matter, (6) repeating steps (3), (4) and (5) if the liquid flooding the matter has not yet reached the temperature required for mesophile methanogenic fermentation of the matter in an anaerobic environment, (7) leaving the liquid in situ once said required temperature has been reached to enable anaerobic mesophile methanogenic fermentation to take place, and (8) collecting the gas given off during such anaerobic fermentation.

2. A method as in claim 1, wherein the temperature required for mesophile methanogenic fermentation lies between 34° and 40° C.

3. A method as in claim 1, further comprising the step of ventilating the fermentable organic matter during steps (1) and (4).

4. A method as in claim 1, wherein the fermentable organic material is heaped.

* * * * *